United States Patent [19]

Akahira et al.

[11] Patent Number: 4,600,432
[45] Date of Patent: Jul. 15, 1986

[54] PROPIONIC ACID DERIVATIVES AND HERBICIDES EMPLOYING THEM

[75] Inventors: Rokuro Akahira, Kurume; Shinzo Someya, Tokorozawa; Mikio Ito, Tokuyama; Akira Nakanishi, Shinnanyo; Yuji Nonaka, Tokuyama, all of Japan

[73] Assignees: Agro-Kanesho Co., Ltd., Tokyo; Toyo Soda Manufacturing Co., Ltd., Shinnanyo, both of Japan

[21] Appl. No.: 758,701

[22] Filed: Jul. 25, 1985

[30] Foreign Application Priority Data

Jul. 25, 1984 [JP] Japan ................ 59-155055
Jun. 24, 1985 [JP] Japan ................ 60-137286

[51] Int. Cl.$^4$ ............... A01N 43/40; A01N 37/34; C07C 121/78
[52] U.S. Cl. .......................... 71/94; 71/100; 71/105; 558/254; 558/414; 546/226
[58] Field of Search ....... 260/453 RW, 455 R, 465 D; 546/226; 71/94, 100, 105

[56] References Cited

U.S. PATENT DOCUMENTS 4,349,377 9/1982 Dürr et al. .................... 71/98
4,394,327 7/1983 Rohr et al. .................... 260/455 R Primary Examiner—Dolph H. Torrence
Attorney, Agent, or Firm—Oblon, Fisher, Spivak, McClelland & Maier

[57] ABSTRACT

Propionic acid derivatives represented by the formula (I)

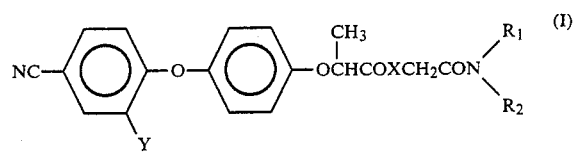

wherein X indicates an oxygen atom or a sulfur atom, Y indicates a hydrogen atom or a halogen atom, $R_1$ and $R_2$ are the same or different group, indicating an alkyl group, alkenyl group, alkynyl group, cycloalkyl group, lower alkoxy group, lower alkoxyalkyl group, phenyl group, respectively, or $R_1$ and $R_2$ may form a heterocyclic group together with a nitrogen atom bonding to said $R_1$ and $R_2$, and herbicidal compositions employing them.

2 Claims, No Drawings

PROPIONIC ACID DERIVATIVES AND HERBICIDES EMPLOYING THEM

FIELD OF THE INVENTION

This invention concerns a novel compound and a selective herbicide containing said compound. More particularly, this invention concerns propionic acid derivatives (hereinafter referred to as "the compound of this invention" represented by the formula (I)

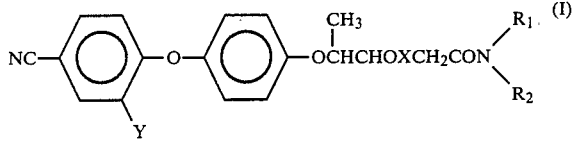

wherein X indicates an oxygen atom or a sulfur atom, Y indicates a hydrogen atom or a halogen atom, $R_1$ and $R_2$ are the same or different group, indicating an alkyl group, alkenyl group, alkynyl group, cycloalkyl group, lower alkoxy group, lower alkoxyalkyl group, phenyl group, respectively, or $R_1$ and $R_2$ may form a heterocyclic group together with a nitrogen atom bonding to said $R_1$ and $R_2$, and herbicidal compositions containing the compound of this invention as an active ingredient.

BACKGROUND OF THE INVENTION

There are already known ester of cyanophenoxyphenoxypropionic acid and herbicides containing this ester as an active ingredient, but a compound made of a conbination of cyanophenoxyphenoxypropionic acid ester and acetic acid amide group are novel ones.

DETAILED DESCRIPTION OF THE INVENTION

The object of this invention lies in providing said compound industrially, and providing active and selective herbicides.

Upon reviewing active and selective herbicides to obtain them, the inventors of this invention have found that some specified propionic acid derivatives can meet the above object to complete this invention.

That is, this invention provides propionic acid derivatives represented by the formula (I)

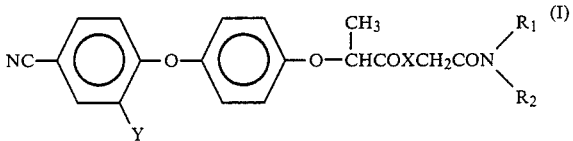

wherein X indicates an oxygen atom or a sulfur atom, Y indicates a hydrogen atom or a halogen atom, $R_1$ and $R_2$ are the same or different group, indicating an alkyl group, alkenyl group, alkynyl group, cycloalkyl group, lower alkoxy group, lower alkoxyalkyl group, phenyl group, respectively, or $R_1$ and $R_2$ may form a heterocyclic group together with a nitrogen atom bonding to said $R_1$ and $R_2$, and providing herbicidal compositions containing the compound of this invention as an active ingredient.

The compounds of this invention can be prepared according to various methods, but typical preparation methods thereof are shown in the following reaction equations, wherein Hal devotes a halogen atom, $R_1$, $R_2$, X, and Y have the same meanings as above respectively.

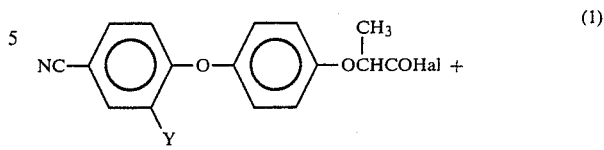

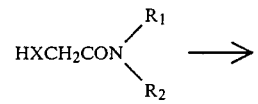

the compound of this invention + H.Hal

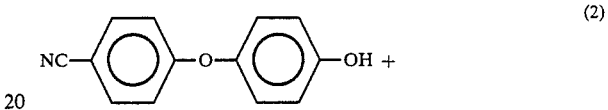

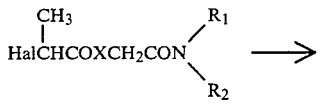

the compound of this invention + H.Hal

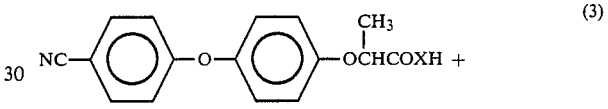

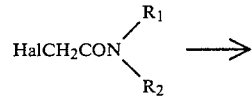

the compound of this invention + H.Hal

Among these methods, the reaction of equation (1) is further explained in detail.

These reactions proceed in the presence of or in the absence of reaction solvent with employing suitable base to give invented compound. As the reaction solvent, ketones such as acetone, methylethylketone and the like, aromatic hydrocarbons such as benzene, toluene, xylene and the like, ethers such as ethylether, tetrahydrofuran, dioxane and the like, halogenated hydrocarbon such as chlorobenzene, chloroform, carbon tetrachloride, dichloroethane and the like, tertiary amine such as triethylamine, pyridine, dimethylaniline and the like, polar solvents such as dimethylformamide, dimethylsulfoxide, phosphoric acid hexamethyltriamide and the like, and so on can be employed.

As the base, tertiary amine such as triethylamine, pyridine, dimethylaniline and the like, alkali metal hydroxide such as sodium hydroxide, potassium hydroxide and the like, alkaline earth metal hydroxide such as calcium hydroxide and the like, alkaline carbonate such as sodium carbonate, potassium carbonate, sodium bicarbonate, potassium bicarbonate and the like and metal hydride such as sodium hydride and the like, and so on can be employed.

The reactions are performed at a reaction temperature of usually about 0° C. to about 150° C., preferably about 20° C. to about 100° C., and over a reaction period from several minutes to about 48 hours.

The compound of this invention can be used as herbicides in form of formulations such as emulsifiable concentrates, water-dispersible powders, powders, granules and the like by admixing various auxiliary agents, for example, dilution agent, solvent, surface active agent and the like. Therewith, for the purpose of lowering labor for scattering or of increasing spectrum of effectively removable weed species, it is sometimes preferable to add other herbicides such as the followings:

2,4-Dichlorophenoxyacetic acid, salts thereof, esters thereof and alkylamine salts thereof.
2-Methyl-4-chlorophenoxyacetic acid, salts thereof and ester thereof.
2-Methyl-4-chlorophenoxybutyric acid, salts thereof and esters thereof.
d,1-2-(4-Chloro-o-tolyloxy)propionic acid, salts thereof and esters thereof.
Octanic acid4-cyano-2,6-diiodophenyl.
2,4-Dichlorophenyl-4'-nitrophenylether.
2,4,6-Trichlorophenyl-4'-nitrophenylether.
2,4-Dichlorophenyl-3'-methoxy-4'-nitrophenylether.
3,4-Dichlorocarbanilidic acid methyl.
3-Chlorocarbanilidic acid isopropyl.
Diethylthiocarbamidic acid-S-4-chlorobenzyl.
4-Nitrophenyl-3',5'-xylylether.
Hexahydro-1H-azepine-1-carbothionic acid-S-ethyl.
3,4-Dichloropropionanilide.
2-Chloro-2',6'-diethyl-N-(butoxymethyl)acetanilide.
2-Chloro-2',6'-diethyl-N-(m-propoxyethyl)acetanilide.
1-(α,α-Dimethylbenzyl)-3-p-tolylurea.
2,4-Bis(ethylamino)-6-methylthio-1,3,5-triazine.
2-Ethylamino-4-isopropylamino-6-methylthio-1,3,5-triazine.
2,4-Bis(isopropylamino)-6-methylthio-1,3,5-triazine.
5-Tert-butyl-3-(2,4,-dichloro-5-isopropoxyphenyl)-1,3,4-oxadiazolin-2-one.
2,6-Dichlorobenzonitrile.
2,6-Dichlorothiobenzamide.
2-Amino-3-chloro-1,4-naphthoquinone.
2,4-Dichlorophenyl-3'-carbomethoxy-4'-nitrophenylether.
N-p-Chlorobenzyloxyphenyl-3,4,5,6-tetrahydrophthalimide.
2,4-Dichlorophenyl-3'-ethoxyethoxy-4'-nitrophenylether.
N-(1-Ethylpropyl)-2,6-dinitro-3,4-xylidine.
4-(2,4-Dichlorobenzoyl)-1,3-dimethyl-pyrazole-5-yl-p-toluenesulfonate.
4-(2,4-Dichlorobenzoyl)-1,3-dimethyl-5-(benzoylmethoxy)pyrazole.
4-(2,4-Dichloro-3-methylbenzoyl)-1,3-dimethyl-5-(benzoylmethoxy)pyrazole.
O,O-Diisopropyl-2-(benzenesulfonamide)-ethylenedithiophosphate.
3,3'-Dimethyl-4-methoxybenzophenone.
α-(2-Naphthoxy)-propionanilide.
O-Ethyl-O-(3-methyl-6-nitrophenyl)-N-sec-butylphosphorothioamidate.
3-Isopropyl-2,1,3-benzothiadiazinone-(4)-2,2-dioxide and salts thereof.
S-(2-Methyl-1-piperizyl-carbonylmethyl)-O,O-di-n-propyldithiophosphate.
S-Benzyl-N,N-dimethylthiocarbamate.

It is possible to provide herbicidal compositions which are active against many weeds species by combining the compound of this invention with one or more than one among these herbicides abovementioned.

[EMBODIMENT OF EXAMPLES]

Next, this invention is explained by employing examples, but this invention is not restricted to only these examples.

EXAMPLE 1

2-[4-(4-Cyanophenoxy)-phenoxy]-propionic acid (N-methyl-N-methoxyaminocarbonyl)methyl ester (compound No. 1)

To the solution of 0.63 g of N-methyl-N-methoxyhydroxyacetic acid amide dissolved in 30 ml of dichloromethane was dropwise added the solution obtained by dissolving 1.6 g of 2-[4-(4-cyanophenoxy)phenoxy]-propionic acid chloride into 10 ml of dichloromethane at room temperature.

After stirring for 10 minutes, 0.53 g of triethylamine was added thereto and this reaction mixture was subjected to stirring at room temperature for 8 hours.

Thereafter, water was added to the reaction mixture in order to separate a solution of dichloromethane. This solution was washed with water, dried over anhydrous magnesium sulfate and the solvent thereof was distilled out. The residue was purified through a column-chromatography [silica gel, benzene/ethyl acetate=10/1 (V/V)] to give 1.35 g of the title compound. The representative examples of invented compound are shown in Table 1 and the elementary analysis data thereof are shown in Table 2.

EXAMPLE 2

Water dispersible powder

A water dispersible powder was prepared by mixing and pulverizing 20 parts (the term "parts" means parts by weight, which is the same hereinafter) of compound No. 6 of this invention, 35 parts of diatomaceous earth, 40 parts of clay, 3 parts of sodium ligninsulfate and 2 parts of sodium dodecylbenzenesulfonate.

EXAMPLE 3

Emulsifiable concentrate

An emulsifiable concentrate was prepared by mixing 20 parts of compound No. 4 of this invention, 72 parts of xylene, 4 parts of polyoxyethylenealkylether and 4 parts of sodium alkylbenzenesulfonate each other to give a homogeneous solution.

TABLE 1

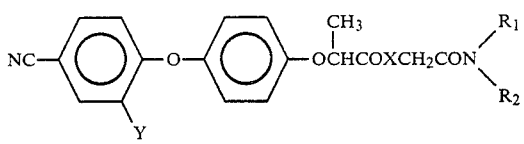

| No. of Compound | X | Y | R₁ | R₂ | Physical constant |
|---|---|---|---|---|---|
| 1 | O | H | —CH₃ | —OCH₃ | $n_D^{25}$ 1.5295 |
| 2 | O | H | —CH₃ | —C₄H₉—n | $n_D^{25}$ 1.5488 |
| 3 | O | H | —CH₃ | —C₆H₁₃—n | $n_D^{25}$ 1.5425 |
| 4 | O | H | —CH₃ | —CH₃ | $n_D^{25}$ 1.5628 |
| 5 | O | H | —C₂H₅ | —C₄H₉—n | $n_D^{25}$ 1.5433 |
| 6 | O | H | —C₄H₉—n | —C₄H₉—n | m.p. 57–60° C. |
| 7 | O | H | —CH₂CH=CH₂ | —CH₂CH=CH₂ | $n_D^{26}$ 1.5539 |
| 8 | O | H | —CH₃ | —C₂H₄—O—CH₃ | $n_D^{25}$ 1.5464 |

TABLE 1-continued

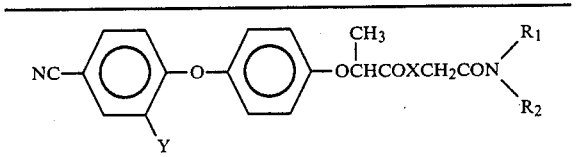

| No. of Compound | X | Y | R₁ | R₂ | Physical constant |
|---|---|---|---|---|---|
| 9 | O | H | —CH₃ | (cyclohexyl-H) | m.p. 61–62.5° C. |
| 10 | O | H | —CH₃ | (cyclopentyl-H) | m.p. 112.5–113° C. |
| 11 | O | H | —C₄H₉—n | —C₆H₁₃—n | $n_D^{25}$ 1.5295 |
| 12 | O | H | —C₆H₁₃—n | —C₆H₁₃—n | $n_D^{25}$ 1.5283 |
| 13 | O | H | —C₈H₁₇—n | —C₈H₁₇—n | $n_D^{25}$ 1.5209 |
| 14 | O | H | (cyclohexyl-H) | (cyclohexyl-H) | m.p. 162–163° C. |
| 15 | O | H | —CH₂C≡CH | —CH₂C≡CH | $n_D^{25}$ 1.5630 |
| 16 | O | H | —N(piperidinyl) | | $n_D^{25}$ 1.5599 |
| 17 | S | H | —CH₃ | —OCH₃ | $n_D^{25}$ 1.5701 |
| 18 | O | H | —CH₃ | (phenyl) | $n_D^{25}$ 1.5752 |
| 19 | O | H | —C₂H₅ | —C₅H₁₁—n | $n_D^{25}$ 1.5382 |
| 20 | O | H | —C₃H₇—i | —C₃H₇—i | m.p. 101–103° C. |

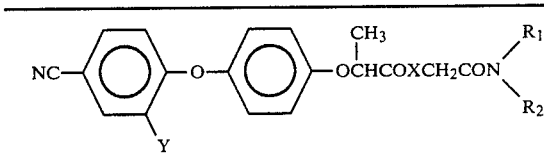

| No. of Compound | X | Y | R₁ | R₂ | Physical constant |
|---|---|---|---|---|---|
| 21 | O | H | —C₂H₅ | (cyclohexyl-H) | $n_D^{25}$ 1.5485 |
| 22 | O | Cl | —CH₃ | —OCH₃ | $n_D^{25}$ 1.5502 |

TABLE 2

| No. of Compound | Molecular formula | Found (%) | Calculated (%) |
|---|---|---|---|
| 1 | C₂₀H₂₀N₂O₆ | C 62.74, H 5.06, N 7.55 | C 62.49, H 5.24, N 7.28 |
| 2 | C₂₃H₂₆N₂O₅ | C 66.91, H 6.33, N 6.81 | C 67.30, H 6.38, N 6.82 |
| 3 | C₂₅H₃₀N₂O₅ | C 68.44, H 6.78, N 6.47 | C 68.47, H 6.89, N 6.38 |
| 4 | C₂₀H₂₀N₂O₅ | C 65.07, H 5.34, N 7.75 | C 65.20, H 5.47, N 7.60 |
| 5 | C₂₄H₂₈N₂O₅ | C 67.98, H 6.58, N 6.58 | C 67.90, H 6.64, N 6.59 |
| 6 | C₂₆H₃₂N₂O₅ | C 68.86, H 7.17, N 6.16 | C 69.00, H 7.12, N 6.19 |
| 7 | C₂₄H₂₄N₂O₅ | C 68.92, H 5.70, N 6.94 | C 68.55, H 5.75, N 6.66 |
| 8 | C₂₂H₂₄N₂O₆ | C 63.69, H 5.96, N 6.56 | C 64.06, H 5.86, N 6.79 |
| 9 | C₂₅H₂₈N₂O₅ | C 68.85, H 6.41, N 6.33 | C 68.79, H 6.46, N 6.41 |
| 10 | C₂₄H₂₆N₂O₅ | C 68.22, H 6.21, N 6.67 | C 68.23, H 6.20, N 6.63 |
| 11 | C₂₈H₃₆N₂O₅ | C 69.92, H 7.72, N 6.12 | C 69.97, H 7.54, N 5.82 |
| 12 | C₃₀H₄₀N₂O₅ | C 71.03, H 7.88, N 5.38 | C 70.84, H 7.92, N 5.50 |
| 13 | C₃₄H₄₈N₂O₅ | C 72.02, H 8.37, N 4.81 | C 72.30, H 8.56, N 4.96 |
| 14 | C₃₀H₃₆N₂O₅ | C 71.64, H 7.10, N 5.46 | C 71.40, H 7.19, N 5.55 |
| 15 | C₂₄H₂₀N₂O₅ | C 69.36, H 4.81, N 6.40 | C 69.22, H 4.84, N 6.72 |
| 16 | C₂₃H₂₄N₂O₅ | C 67.27, H 5.88, N 6.51 | C 67.63, H 5.92, N 6.85 |
| 17 | C₂₀H₂₀N₂O₅S | C 60.13, H 4.96, N 6.89 | C 59.98, H 5.03, N 6.99 |
| 18 | C₂₅H₂₂N₂O₅ | C 69.73, H 4.98, N 6.40 | C 69.75, H 5.15, N 6.50 |
| 19 | C₂₅H₃₀N₂O₅ | C 68.33, H 6.70, N 6.64 | C 68.47, H 6.89, N 6.38 |
| 20 | C₂₄H₂₈N₂O₅ | C 68.28, H 6.82, N 6.40 | C 67.90, H 6.64, N 6.59 |
| 21 | C₂₆H₃₀N₂O₅ | C 69.55, H 6.59, N 6.07 | C 69.31, H 6.71, N 6.21 |
| 22 | C₂₀H₁₉ClN₂O₆ | C 57.43, H 4.69, N 6.75 | C 57.35, H 4.57, N 6.68 |

EXAMPLE 4

Granules

After 5 parts of compound No. 1 of this invention, 3 parts of white carbon, 22 parts of bentonite, 42.5 parts of talc, 25 parts of clay, 2 parts of sodium ligninsulfonate and 0.5 part of sodium dodecylbenzenesulfonate were admixed uniformly and then added with water, the resulted mixture was formed into a granular type through an extruding granulator, which was followed by drying and separating through a sieve to give granules. Next, herbicidal activities of the drugs of this invention are explained by the following test examples.

EXAMPLE 5

Activity test against barnyard grass

After paddy field soils were filled respectively into Wagner pots having a diameter "one five thousandth are" and then puddled, 50 particles of barnyard grass seed were sown thereon. Flooded condition with 3 cm in depth was kept, at the time of germination and 1.5 leaf stage of barnyard grass, designed amounts of the emulsifiable concentrate, which were previously prepared from the compound of this invention according to Example 3, were diluted with water beforehand and then treated uniformly on the water surface of each pots.

On 15th day after the treatment by these drugs, the herbicidal activities against barnyard grass thereof were examined to afford the results of Table 3.

TABLE 3

| Compound No. | Effective dose kg/ha | | | |
|---|---|---|---|---|
| | Barnyard grass in germination stage | | Barnyard grass in 1.5-leaf stage | |
| | 0.25 | 0.06 | 4 | 1 |
| 1 | 5 | 5 | 5 | 5 |
| 2 | 5 | 4–5 | 5 | 5 |
| 3 | 4 | 2–3 | 4 | 3 |
| 4 | 5 | 4 | 5 | 4 |
| 5 | 5 | 5 | 5 | 5 |
| 6 | 5 | 5 | 5 | 5 |
| 7 | 5 | 5 | 5 | 5 |
| 8 | 5 | 5 | 5 | 4–5 |
| 9 | 5 | 5 | 5 | 4 |
| 10 | 4–5 | 3 | 4 | 3 |
| 11 | 5 | 4 | 4 | 3 |
| 12 | 4–5 | 2–3 | 5 | 3 |
| 13 | 3 | 2 | 3 | 2 |
| 14 | 4–3 | 2 | 3 | 2 |
| 15 | 4 | 3 | 4 | 2–3 |
| 16 | 5 | 4 | 5 | 3 |
| 17 | 5 | 3 | 5 | 4 |
| 18 | 4 | 2 | 5 | 5 |
| 19 | 5 | 4–5 | 5 | 5 |
| 20 | 4–5 | 3 | 4 | 2 |
| 21 | 5 | 3 | 5 | 4–5 |
| 22 | 5 | 5 | 5 | 5 |
| Not treated | 0 | 0 | 0 | 0 |

The herbicidal activities were evaluated by the following standard.

| Index of Weed Control | Herbicidal Activities |
|---|---|
| 5 | Killed |
| 4 | 80–99% Prevention |
| 3 | 60–79% Prevention |
| 2 | 40–59% Prevention |
| 1 | 20–39% Prevention |
| 0 | No Prevention |

EXAMPLE 6

Prevention test of barnyard grass under water-seeded rice condition

After paddy field soils were filled respectively into Wagner pots having a diameter "one five thousandth are" and then puddled 20 particles of rice plant seed (Variety: Nihonbare) and 50 particles of barnyard grass seed were sown thereon. At the time of germinations of the rice plant seeds and the barnyard grass seeds, designed amounts of the emulsifiable concentrate, which were previously prepared from the compound of this invention according to Example 3, were diluted with water and then treated uniformly on the water surface of each flooded pots, in which water depth was kept to be 3 cm respectively, for treatment thereof.

On 14th day after the treatment by these dilutions, on herbicidal activities and phytotoxicities were examined to give the results of Table 4.

[Effect of the Invention]

The compound of this invention showed strong herbicidal activities against barnyard grass which is a weed having bad effectiveness in cultivation of rice plant.

On the other hand, the compound of this invention showed herbicidal selectivities on barnyard grass in any stage from directly sown to transplanted and so on.

TABLE 4

| Compound No. | Rice plant or Barnyard grass | Effective dose kg/ha | |
|---|---|---|---|
| | | 1 | 0.25 |
| 1 | Rice plant | 100 | 100 |
| | Barnyard grass | 0 | 0 |
| 2 | Rice plant | 94 | 100 |
| | Barnyard grass | 0 | 0 |
| 3 | Rice plant | 86 | 100 |
| | Barnyard grass | 0 | 14 |
| 4 | Rice plant | 100 | 100 |
| | Barnyard grass | 0 | 0 |
| 5 | Rice plant | 90 | 100 |
| | Barnyard grass | 0 | 0 |
| 6 | Rice plant | 94 | 100 |
| | Barnyard grass | 0 | 0 |
| 7 | Rice plant | 100 | 100 |
| | Barnyard grass | 0 | 0 |
| 8 | Rice plant | 100 | 100 |
| | Barnyard grass | 0 | 0 |
| 9 | Rice plant | 90 | 100 |
| | Barnyard grass | 0 | 0 |
| 10 | Rice plant | 100 | 100 |
| | Barnyard grass | 0 | 0 |
| 11 | Rice plant | 100 | 100 |
| | Barnyard grass | 0 | 0 |
| 12 | Rice plant | 89 | 100 |
| | Barnyard grass | 0 | 0 |
| 13 | Rice plant | 83 | 100 |
| | Barnyard grass | 13 | 31 |
| 14 | Rice plant | 58 | 100 |
| | Barnyard grass | 31 | 46 |
| 15 | Rice plant | 100 | 100 |
| | Barnyard grass | 0 | 19 |
| 16 | Rice plant | 100 | 100 |
| | Barnyard grass | 0 | 0 |
| 17 | Rice plant | 100 | 100 |
| | Barnyard grass | 0 | 0 |
| 18 | Rice plant | 96 | 100 |
| | Barnyard grass | 0 | 18 |
| 19 | Rice plant | 94 | 100 |
| | Barnyard grass | 0 | 0 |
| 20 | Rice plant | 100 | 100 |
| | Barnyard grass | 0 | 0 |
| 21 | Rice plant | 100 | 100 |
| | Barnyard grass | 0 | 0 |
| 22 | Rice plant | 100 | 100 |
| | Barnyard grass | 0 | 0 |
| Not treated | Rice plant | 100 | 100 |
| | Barnyard grass | 100 | 100 |

What is claimed is:

1. Propionic acid derivatives represented by the formula (I)

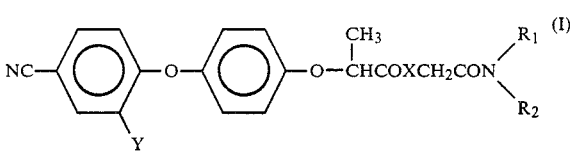

wherein X indicates an oxygen atom or a sulfur atom, Y indicates a hydrogen atom or a halogen atom, $R_1$ and $R_2$ are the same or different group, indicating an alkyl group, alkenyl group, alkynyl group, cycloalkyl group, lower alkoxy group, lower alkoxyalkyl group, phenyl group, respectively, or $R_1$ and $R_2$ may form a heterocyclic group together with a nitrogen atom bonding to said $R_1$ and $R_2$.

2. Herbicidal compositions containing at least one of propionic acid derivatives represented by the formula (I)

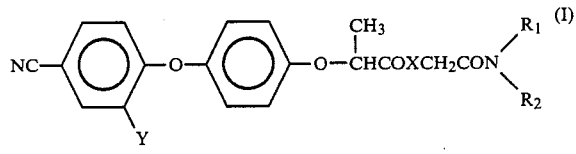

wherein X indicates an oxygen atom or a sulfur atom, Y indicates a hydrogen atom or a halogen atom, $R_1$ and $R_2$ are the same or different group, indicating an alkyl group, alkenyl group, alkynyl group, cycloalkyl group, lower alkoxy group, lower alkoxyalkyl group, phenyl group, respectively, or $R_1$ and $R_2$ may form a heterocyclic group together with a nitrogen atom bonding to said $R_1$ and $R_2$, as an active ingredient.

* * * * *